(12) United States Patent
Barkhordar

(10) Patent No.: US 8,668,397 B2
(45) Date of Patent: Mar. 11, 2014

(54) PORTABLE TOOTHBRUSH FOR DELIVERING AND REMOVING FLUID

(76) Inventor: Afsoon Barkhordar, Los Angeles, CA (US)

(*) Notice: Subject to any disclaimer, the term of this patent is extended or adjusted under 35 U.S.C. 154(b) by 430 days.

(21) Appl. No.: 13/107,200

(22) Filed: May 13, 2011

(65) Prior Publication Data

US 2012/0288320 A1 Nov. 15, 2012

(51) Int. Cl.
*A47L 13/26* (2006.01)
*B43K 5/02* (2006.01)

(52) U.S. Cl.
USPC ........... 401/13; 401/188 R; 401/282; 15/22.1; 15/29; 15/320

(58) Field of Classification Search
USPC ........... 401/13, 188 R, 189, 282; 15/22.1, 24, 15/29, 320, 321, 322, 344; 433/84, 88, 89
See application file for complete search history.

(56) References Cited

U.S. PATENT DOCUMENTS

| | | | | |
|---|---|---|---|---|
| 5,458,563 A * | 10/1995 | Stewart | ........................ | 601/162 |
| 6,047,429 A * | 4/2000 | Wu | ................................ | 15/29 |
| 6,336,428 B1 * | 1/2002 | Locke | .......................... | 119/625 |
| 7,448,109 B2 * | 11/2008 | Brewer et al. | .................. | 15/22.1 |
| 2003/0208145 A1 * | 11/2003 | Stewart | ........................ | 601/162 |
| 2005/0066456 A1 * | 3/2005 | Gavney, Jr. | .................... | 15/22.1 |
| 2011/0067193 A1 * | 3/2011 | Olson | ........................ | 15/167.1 |

* cited by examiner

*Primary Examiner* — David Walczak
*Assistant Examiner* — Jennifer C Chiang
(74) *Attorney, Agent, or Firm* — Adli Law Group P.C.

(57) ABSTRACT

A hand-held portable electric or manual toothbrush that is capable of delivering and removing fluid while the toothbrush is being used. A fluid delivery tube delivers fluid from a clean fluid repository to the head of the toothbrush. A fluid removal tube removes used fluid from the user's mouth. The clean fluid is delivered via a pump positioned within a cavity of the toothbrush. The used fluid is removed via a vacuum positioned within the cavity of the toothbrush. This invention enables everyone, including the young, elderly, busy, healthy, sick, disabled, handicapped, and immobile, to brush anytime and anywhere. As a result, this invention would greatly improve the oral health of the general population.

9 Claims, 2 Drawing Sheets

PORTABLE TOOTHBRUSH FOR DELIVERING AND REMOVING FLUID

FIELD OF THE INVENTION

The present invention relates to a portable toothbrush apparatus that can be operated either electrically or manually. Specifically, the present invention relates to a portable toothbrush capable of delivering and removing fluid while the toothbrush is being used. The toothbrush can be used by any person, at any time, at any location and does not need to be used near a water source. This invention would improve the oral health of the general population because everyone, including the young, elderly, busy, healthy, sick, handicapped, disabled, and immobile will be able to brush anytime and anywhere. Those who are unable to walk to the sink, in nursing homes, stuck in bed can brush more readily and independently. This invention would also help people on the run brush at work, right after lunch or right before a meeting and at the convenience of their offices or even their vehicles. The invention is just as portable as a man's razor or shaver and the convenience that it has to offer would improve the oral health of the general population.

BACKGROUND

Portable electric or manual toothbrushes in the prior art are well known. They have been used throughout the years as oral hygiene instruments used to clean teeth and gums.

The first successful electric toothbrush was produced in 1939 in Switzerland by Dr. Philippe-Guy Wong. The electrical toothbrush was first marketed in the United States in 1959 by E. R. Squibb. The brush was called the Broxodent. General Electric introduced a rechargeable cordless toothbrush in 1961. Interplak was the first rotary action electrical toothbrush for home use, introduced in 1987.

Electric toothbrushes have gained in popularity over the years due to their inherent benefits. For example, electric toothbrushes move their bristles at a much faster rate than is possible by the human hand. As such, electric toothbrushes can provide a deeper cleaning in a shorter period of time as compared to traditional manual toothbrushes.

As another example, bristles from an electric toothbrush can easily be held against teeth and gums in hard-to-reach areas of the mouth. As such, additional bristle strokes can be applied to those hard-to-reach areas of the mouth without any additional effort on the part of the user. This again helps to provide deeper teeth cleanings each time a user brushes his or her teeth.

As yet another example, people with limited manual dexterity may find it difficult to manually brush their teeth. For these people, electric toothbrushes provide a much better and easier method of cleaning their teeth as compared to traditional toothbrushes.

Electronic toothbrushes come in many forms. Nevertheless, they can generally be described as including a head section and a body section. The head section includes a multiplicity of bristles, which is attached to an end of the body section. The body section can be held by the user when brushing his or her teeth. The body section also typically houses a motor powered by a rechargeable battery. The motor drives the actions of the bristles when the electronic toothbrush is in use.

SUMMARY

According to the embodiments of the present invention, a portable electric or manual toothbrush is provided that is capable of delivering and removing fluid while the toothbrush is being used.

One object of the present invention is to provide an improved portable manual toothbrush that can deliver and remove fluid from the user's mouth via the head of the electric toothbrush.

Another object of the present invention is to provide an improved portable electric toothbrush powered by a rechargeable battery that can deliver and remove fluid from the user's mouth via the head of the electric toothbrush.

In an embodiment, the portable electric or manual toothbrush includes a toothbrush head having a multiplicity of bristles. The toothbrush head is attached to a first end of a handle having a cavity for accommodating, among other things, a pump, a vacuum, a clean fluid repository, and a used fluid repository. For electric toothbrushes, the toothbrush head is also attached to a battery power source and a motor.

In an embodiment, a motor is used to move the bristles positioned on the toothbrush head. In an embodiment, one or more groups of bristles are rotated about a central axis via the motor. In another embodiment, the motor is used to oscillate the multiplicity of bristles on the toothbrush head.

In an embodiment, clean fluid (e.g., water, liquid toothpaste, mouthwash, prescription antibacterial or antimicrobial rinse) is delivered from the clean fluid repository to the toothbrush head through a fluid delivery tube. In an embodiment, the pump located within the handle supplies the necessary pressure to the clean fluid to deliver it to the toothbrush head. In an embodiment, the end of the fluid delivery tube located proximal to the toothbrush head is placed adjacent to the bristles, wherein the exposed portion of fluid delivery tube extends away from the base of the toothbrush head parallel with the bristles.

In an embodiment, the used fluid is delivered from the user's mouth to the used fluid repository through a fluid recovery tube. In an embodiment, the vacuum pump and/or motor located within the cavity of the handle supplies the necessary pressure to suck the used fluid from the user's mouth to the used fluid repository. In an embodiment, the end of the fluid recovery tube located proximal to the toothbrush head is placed adjacent to the bristles, wherein the exposed end of fluid recovery tube extends away from the base of the toothbrush head parallel with the bristles.

In use, fluid can be delivered to and retrieved from the user's mouth while the user is brushing his or her teeth. This self-contained fluid-filled tooth brushing device allows the user to easily brush his or her teeth away from a permanent water source (e.g., a sink). This may be beneficial if the user is immobile and cannot move him or herself to the permanent water source, or if there is no permanent water source that is readily available.

In use, the toothbrush can benefit the elderly, those in nursing homes, people on the run, etc. Users can brush after lunch, right before a meeting, etc, which improves the oral health of the general population. It is just as portable as a man's razor or shaver.

BRIEF DESCRIPTION OF THE DRAWINGS

The accompanying drawings, which are incorporated into and constitute a part of this specification, illustrate one or more embodiments, and together with the detailed description, serve to explain the principles and implementations of the invention. In the drawings.

DETAILED DESCRIPTION

Embodiments are described herein in the context of a portable electric or manual toothbrush capable of delivering and removing fluid. Those of ordinary skill in the art will realize that the following detailed description is illustrative only and is not intended to be in any way limiting. Other embodiments of the present invention will readily suggest themselves to such skilled persons having the benefit of this disclosure. Reference will now be made in detail to implementations of embodiments of the present invention as illustrated in the accompanying drawings. The same reference indicators will be used throughout the drawings and the following detailed description to refer to the same or like parts.

Figure 1:
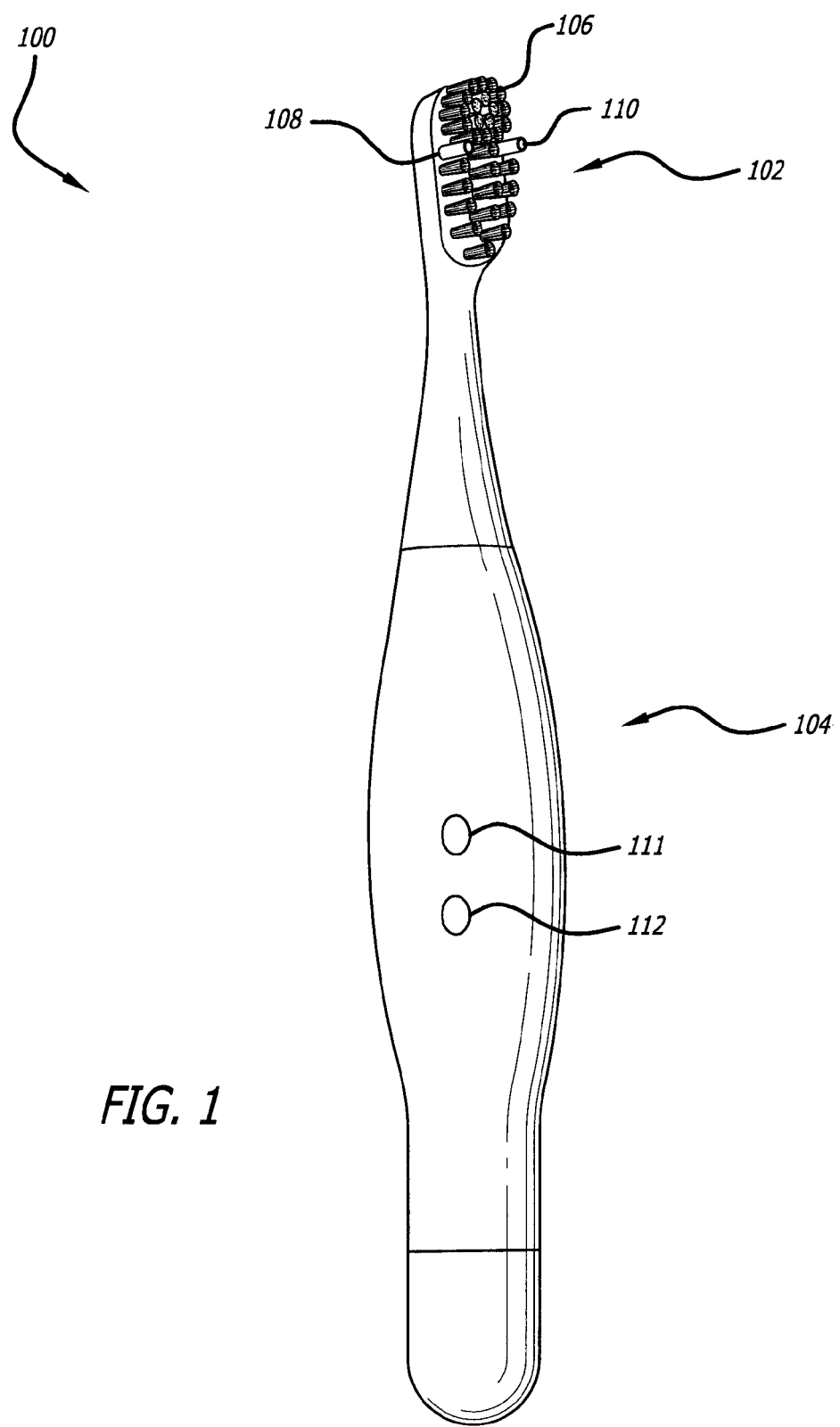
FIG. 1 illustrates a front view of a portable toothbrush in accordance with an embodiment of the present invention.

Referring now to FIG. 1, a portable toothbrush capable of delivering and removing fluid in accordance with an embodiment of the invention is illustrated. Specifically, FIG. 1 illustrates portable toothbrush 100 generally including head section 102 and body section 104. In this embodiment, head section 102 depicts a toothbrush head that includes a multiplicity of bristles 106, a fluid feed tube 108, and a fluid removal tube 110. In an embodiment, the multiplicity of bristles can be mechanically manipulated to clean the user's teeth in any manner as envisioned by one having ordinary skill in the art. For example, the bristles can be rotated, they can be moved back and forth, and/or they can be oscillated as a part of toothbrush head 106. In an embodiment of the invention, the multiplicity of bristles may even be positioned in a stationary manner so that portable toothbrush 100 is used in the same manner as a traditional, non-electronic toothbrush. Furthermore, body section 104 serves as the handle for portable toothbrush 100 and as a place to hold other parts or the toothbrush, such as the motor, pump, vacuum, battery, reservoirs, tubes, etc.

In this embodiment of the invention, head section 102 is detachable and can be replaced when the bristles fall out, get worn out, or require replacement. In this embodiment of the invention, head section 102 can further be seen as including fluid feed tube 108 and fluid removal tube 110. Fluid feed tube 108 can be used to deliver a fluid (e.g., water, liquid toothpaste, mouthwash, prescription antibacterial or antimicrobial rinse) to the user's mouth while portable toothbrush 100 is in use. As the user is brushing his or her teeth, fluid removal tube 110 can simultaneously be used to suck the used fluid out of the user's mouth.

In an embodiment of the invention, the end of fluid delivery tube 108 located proximal to toothbrush head 106 is positioned adjacent to the bristles, wherein the exposed portion of fluid delivery tube 108 extends away from the base of toothbrush head 106 parallel to the bristles. Similarly, in an embodiment, the end of fluid removal tube 110 located proximal to toothbrush head 106 is positioned adjacent to the bristles, wherein the exposed end of fluid removal tube 110 extends away from the base of toothbrush head 106 parallel to the bristles. The exposed ends of fluid delivery tube 108 and fluid removal tube 110 can have any length. In an embodiment, the lengths of the exposed ends of fluid delivery tube 108 and fluid removal tube 110 are approximately the same as the lengths of the bristles. In an embodiment, fluid delivery tube 108 and fluid removal tube 110 should either be flexible and/or shorter so that they will not interfere with the brushing process.

In another embodiment, the toothbrush can have an on/off button or switch 111. In yet another embodiment, the toothbrush can have a button or switch 112 that allows the user to select whether to run the toothbrush manually or electrically.

Figure 2:
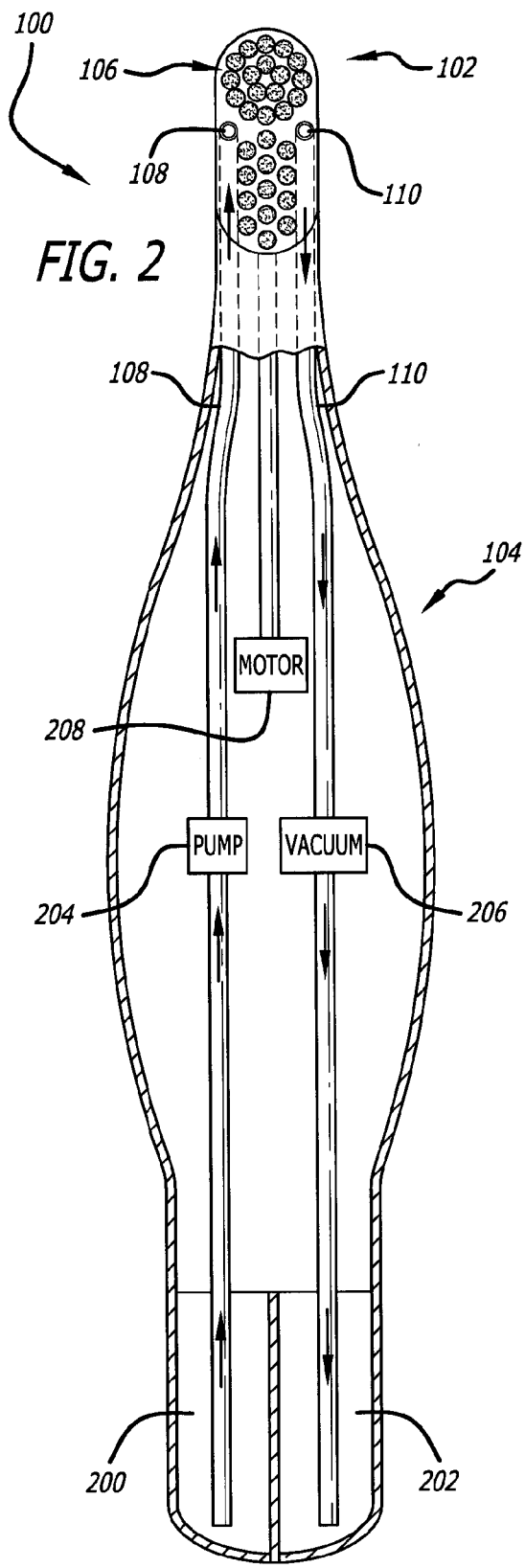
FIG. 2 illustrates a conceptual cross-sectional view of a portable toothbrush in accordance with an embodiment of the present invention.

Referring now to FIG. 2, a conceptual front cross-sectional view of portable toothbrush 100 is illustrated. Here, fluid feed tube 108 can be seen as extending from head section 102, through the entire length of portable toothbrush 100, and into clean fluid repository 200. In this embodiment, clean fluid repository 200 is positioned at the base of body section 104. Body section 104 serves as the space for the motor 208, the pump 204, the battery, etc. Similarly, fluid removal tube 110 can be seen as extending from head section 102, through the entire length of portable toothbrush 100, and into used fluid repository 202. In this embodiment, used fluid repository 202 is positioned at the base of body section 104. In an embodiment, clean fluid repository 200 and used fluid repository 202 are both removably attached to portable toothbrush 100 so that clean fluid can readily be placed in clean fluid repository 200, and used fluid can readily be removed from used fluid repository 202. In an embodiment, clean fluid repository 200 can be removed, washed, and filled with clean water, mouthwash, or prescription antibacterial mouth rinse, such as Peridex, Chlorohexidine, etc. In an embodiment, used fluid repository 202 can be removed, emptied of the used fluid contained within, washed, cleaned, and re-inserted back in the body section 104.

In an embodiment of the invention, the clean fluid repository 200 and the used fluid repository 202 can be made and purchased as a separate unit if the user does not wish to wash or clean them. The new replacement used fluid repository 202 can be inserted and the old fluid repository can be replaced and disposed of. Furthermore, the clean fluid repository 200 can be filled with different fluids, including but not limited to plain water, prescription antibacterial or antimicrobial rinse, such as Peridex or Chlorohexidine, which can be purchased readily and inserted in body section 104.

Still referring to FIG. 2, pump 204 and vacuum 206 can generally be seen as being incorporated into a cavity of body section 104 of portable toothbrush 100. In use, pump 204 provides the necessary pressure to force clean fluid obtained from clean fluid repository 200 through fluid feed tube 108 and into the user's mouth. Along the same lines, vacuum 206 provides the necessary suction pressure to withdraw used fluid from the user's mouth, through fluid removal tube 110, and into used fluid repository 202. It is to be understood that pump 204 and vacuum 206 are not intended to be limited to any specific implementations or mechanisms, and that any appropriate implementations or mechanisms can be used within portable toothbrush 100 that would be known to one having ordinary skill in the art. In an embodiment, the pump and vacuum may constitute one combined device that is capable of performing both functions. Furthermore, it is also to be understood that pump 204 and vacuum 206 can be positioned at any location within portable toothbrush 100.

In an embodiment of the invention, motor 208 can also be provided. Motor 208 can be used to drive the movement of the multiplicity of bristles located on toothbrush head 106. Once again, it is to be understood that motor 208 is not intended to be limited to any specific implementation or mechanism, and that any appropriate implementation or mechanism can be used to drive the movement of the multiplicity of bristles located on toothbrush head 206. These implementations would be known to those having ordinary skill in the art.

Figure 3A:
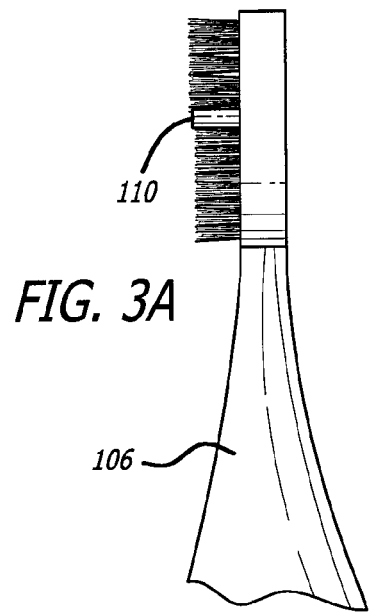
FIGS. 3A and 3B illustrate side views of the toothbrush head of a portable toothbrush in accordance with embodiments of the present invention.
Figure 3B:
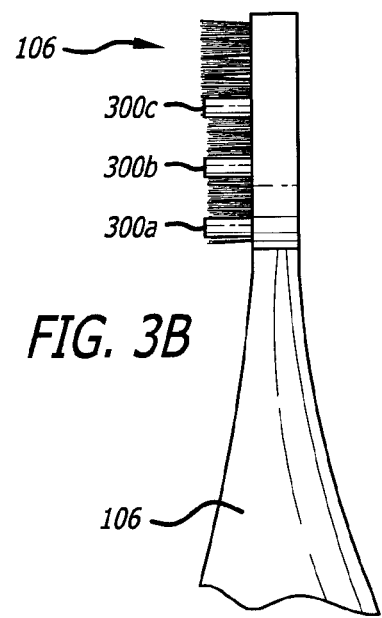

Referring now to FIG. 3A, a side view of an embodiment of toothbrush head 106 is illustrated. Here, portable toothbrush 100 includes one fluid removal tube 110 and one fluid feed tube 108 (not shown). Nevertheless, in other embodiments, the fluid feed tube and the fluid removal tubes can have a plurality of exposed ends. For example, FIG. 3B illustrates a side view of an embodiment of toothbrush head 106 wherein fluid removal tube 110 includes three separate exposed ends 300a, 300b, 300c. In alternative embodiments, fluid removal tube 110 and fluid feed tube 108 may have more or less exposed ends on toothbrush head 106. In other embodiments, the exposed ends of fluid removal tube 110 and fluid feed tube 108 may be positioned at any location on toothbrush head 106. For example, they may be located in at the center of toothbrush head 106.

Portable toothbrush 100 can also have various other elements as would be envisioned by one having ordinary skill in the art. The user can select to operate the toothbrush either manually or electrically. For example, in an embodiment, pump 204, vacuum 206 and motor 208 are all powered by a battery. In the preferred embodiment of the invention, the battery is rechargeable. In another embodiment of the invention, the battery can be replaced overtime. The battery can be purchased as a separate unit and inserted when the battery is no longer rechargeable.

In an embodiment of the invention, portable toothbrush 100 may have one button or switch 112 that can be selected by the user to cause movement of the multiplicity of bristles on toothbrush head 106. The user can then select another on/off button or switch 111 to initiate the process of pumping fluid into the user's mouth, as well as vacuuming used fluid out of the user's mouth. In another embodiment, three separate buttons or switches can be used that control motor 208, vacuum 206 and pump 204 independently. In one embodiment, the toothbrush can also be designed to have one button to activate or operate all three functions/buttons/switches.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modification that are suited to the particular use contemplated. It is intended that the scope of the invention be defined by the claims and their equivalents.

What is claimed is:

1. A portable electric or manual toothbrush comprising: a head comprising a multiplicity of bristles; a handle including a cavity, wherein the head is attached to a first end of the handle, wherein the cavity houses a motor, a pump, a vacuum, a clean fluid repository, and a used fluid repository; a fluid delivery tube and a fluid removal tube, wherein the fluid delivery tube extends from the clean fluid repository to the head, wherein the fluid removal tube extends from the used fluid repository to the head; wherein the fluid delivery tube delivers clean fluid from the clean fluid repository to the head through the use of the pump; and wherein the fluid removal tube delivers used fluid from the head to the used fluid repository through the use of the vacuum.

2. The portable electric or manual toothbrush of claim 1, further comprising: a rechargeable battery housed within the cavity, wherein the rechargeable battery provides power to the pump and the vacuum.

3. The portable electric or manual toothbrush of claim 1, further comprising: an on/off switch that controls the motor, pump, and vacuum.

4. The portable electric or manual toothbrush of claim 1, further comprising: an on/off switch to that allows the user to select whether to operate the toothbrush manually or electrically.

5. The portable electric or manual toothbrush of claim 1: wherein a first end of the fluid delivery tube located adjacent to the head extends away from a base of the head parallel to the multiplicity of bristles.

6. The portable electric or manual toothbrush of claim 1: wherein a first end of the fluid removal tube located adjacent to the head extends away from a base of the head parallel to the multiplicity of bristles.

7. The portable electric or manual toothbrush of claim 1: wherein the multiplicity of bristles are mechanically moveable using a motor located within the cavity of the handle.

8. The portable electric or manual toothbrush of claim 3: wherein the fluid delivery tube comprises a plurality of exposed ends that extend away from the base.

9. The portable electric or manual toothbrush of claim 4: wherein the fluid removal tube comprises a plurality of exposed ends that extend away from the base.

* * * * *